(12) United States Patent
Al-Yami et al.

(10) Patent No.: US 10,577,300 B2
(45) Date of Patent: Mar. 3, 2020

(54) SYNTHESIS OF SODIUM FORMATE AND DRILLING FLUID COMPRISING THE SAME

(71) Applicant: Saudi Arabian Oil Company, Dhahran (SA)

(72) Inventors: Abdullah Al-Yami, Dhahran (SA); Vikrant Wagle, Abqaiq (SA); Zainab Alsaihati, Saihat (SA); Ali Alsafran, Dhahran (SA); Nasser Alalhareth, Ras Tanura (SA); Abdulaziz Alhelal, Alhsa Hofuf (SA)

(73) Assignee: Saudi Arabian Oil Company, Dhahran (SA)

( * ) Notice: Subject to any disclaimer, the term of this patent is extended or adjusted under 35 U.S.C. 154(b) by 67 days.

(21) Appl. No.: 16/006,225

(22) Filed: Jun. 12, 2018

(65) Prior Publication Data

US 2019/0375700 A1    Dec. 12, 2019

(51) Int. Cl.
*C07C 51/41* (2006.01)
*B01J 19/24* (2006.01)
(Continued)

(52) U.S. Cl.
CPC .............. *C07C 51/412* (2013.01); *B01J 19/24* (2013.01); *C07C 51/43* (2013.01); *C07C 51/47* (2013.01);
(Continued)

(58) Field of Classification Search
CPC ....... C07C 51/412; C07C 51/43; C07C 51/47; C07C 51/48; B01J 19/00; B01J 19/24; B01J 2219/00186
See application file for complete search history.

(56) References Cited

U.S. PATENT DOCUMENTS 3,968,176 A    7/1976  Uehama et al.
4,277,620 A    7/1981  Gupton et al.
(Continued)

FOREIGN PATENT DOCUMENTS

CN    104962255 A    10/2015
WO    94/09253 A1    4/1994
(Continued)

OTHER PUBLICATIONS

International Search Report and Written Opinion dated Apr. 11, 2019 pertaining to International application No. PCT/US2018/056179 filed Oct. 17, 2018, 19 pgs.

*Primary Examiner* — Lessanework Seifu
(74) *Attorney, Agent, or Firm* — Dinsmore & Shohl LLP (57) ABSTRACT

A method of synthesizing sodium formate. The method includes reacting acetaldehyde, formaldehyde, and NaOH to form a raw reaction solution which includes pentaerythritol and sodium formate. The method also includes passing the raw reaction solution to an evaporator to reduce the water content of the raw reaction solution and remove any unreacted formaldehyde from the raw reaction solution to form a concentrated reaction solution and cooling the concentrated reaction solution to form pentaerythritol crystals in suspension while retaining sodium formate in solution. Further, the method includes filtering the cooled concentrated reaction solution to remove the pentaerythritol crystals and create a mother liquor comprising the sodium formate in solution and separating the sodium formate from the mother liquor.

8 Claims, 3 Drawing Sheets

(51) Int. Cl.
*C07C 51/47* (2006.01)
*C07C 51/43* (2006.01)
*C09K 8/035* (2006.01)
*C07C 51/48* (2006.01)

(52) U.S. Cl.
CPC .............. *C07C 51/48* (2013.01); *C09K 8/035* (2013.01); *B01J 2219/00186* (2013.01)

(56) References Cited

U.S. PATENT DOCUMENTS

| | | |
|---|---|---|
| 4,327,070 A | 4/1982 | Meyers |
| 5,804,535 A | 9/1998 | Dobson et al. |
| 2010/0152500 A1 | 6/2010 | Jiang et al. |
| 2014/0066339 A1 | 3/2014 | Tej et al. |

FOREIGN PATENT DOCUMENTS

| | | |
|---|---|---|
| WO | 99/48994 A1 | 9/1999 |
| WO | 03052024 A1 | 6/2003 |
| WO | 2005012456 A1 | 2/2005 |
| WO | 2008096147 A1 | 8/2008 |
| WO | 2014133824 A1 | 9/2014 |
| WO | 2016140698 A1 | 9/2016 |
| WO | 2017147712 A1 | 9/2017 |

SYNTHESIS OF SODIUM FORMATE AND DRILLING FLUID COMPRISING THE SAME

TECHNICAL FIELD

Embodiments of the present disclosure generally relate to methods and related system for synthesizing sodium formate and drilling fluid compositions using the sodium formate. More specifically, embodiments of the present disclosure generally relate to methods of synthesizing sodium formate from acetaldehyde, formaldehyde, and sodium hydroxide.

BACKGROUND

Drilling fluids are commonly utilized in the drilling of subterranean oil and gas wells. In rotary drilling operations drilling fluids, also known as drilling muds, or simply "muds", provide a variety of functions and performance enhancements. Initially the drilling fluid carries cuttings away from the cutting bit and transports them to the surface of the wellbore for separation. The drilling fluid also provides cooling functionality for the bit as the drilling fluid is flowed throughout the wellbore. A drilling mud is provided to reduce friction between the drill string and the sides of the wellbore while maintaining the stability of the walls of the wellbore. Specifically, the drilling fluid is formulated to prevent incursion of formation fluids from surrounding rocks or excursion of the drilling fluid into the surrounding rocks.

Drilling fluids have been developed which utilize sodium formate as a constituent component. Sodium formate has been traditionally utilized in drilling fluids for its health, safety, and environmental (HSE) profile and its compatibility with reservoir fluids, function as a good shale stabilizer, function as a gas hydrate inhibitor, and function as a scale dissolver.

Sodium formate is traditionally synthesized by the reaction of carbon monoxide with sodium hydroxide at 150-170° C. and about 2 megapascal (MPa). Sodium formate may also be produced by the reaction of formic acid with oxygen or sodium bicarbonate. However, traditional methods of forming sodium formate provide sodium formate of limited purity, generally up to 98 weight percent (wt. %) pure, resulting in reduced performance when utilized in a drilling fluid.

SUMMARY

As such, there is an ongoing need for ultra-pure sodium formate having a purity in excess of 99.5% wt. %. For purposes of this disclosure, "ultra-pure sodium formate" comprises sodium formate with purity in excess of 99.5 wt. %.

Embodiments of the present disclosure are directed to methods of synthesizing ultra-pure sodium formate and drilling fluid compositions comprising the ultra-pure sodium formate.

According to an aspect, a method of synthesizing ultra-pure sodium formate includes reacting acetaldehyde, formaldehyde, and NaOH to form a raw reaction solution. The raw solution includes pentaerythritol and sodium formate. The method also includes reducing the water content of the raw reaction solution and removing unreacted formaldehyde from the raw reaction solution to form a concentrated reaction solution with a formaldehyde concentration less than 0.5% by weight. Additionally, the method includes cooling the concentrated reaction solution to form pentaerythritol crystals in suspension while retaining the sodium formate in solution as a crystallized pentaerythritol solution. The method also includes filtering the crystallized pentaerythritol solution to remove the pentaerythritol crystals and create a mother liquor with the sodium formate in solution and separating the sodium formate from the mother liquor to collect sodium formate having a purity in greater than 99.5 wt. %.

According to another aspect, a system for synthesizing ultra-pure sodium formate includes a reaction vessel having one or more inlets connected to an acetaldehyde feed stream, a formaldehyde feed stream, and a NaOH feed stream. The reaction vessel is configured to react acetaldehyde, formaldehyde, and NaOH from the acetaldehyde feed stream, the formaldehyde feed stream, and the NaOH feed stream respectively to form a raw reaction solution. The raw reaction solution includes pentaerythritol and sodium formate. The system also includes an evaporator downstream of the reaction vessel. The evaporator is configured to reduce the water content of the raw reaction solution and remove unreacted formaldehyde from the raw reaction solution to form a concentrated reaction solution with a formaldehyde concentration less than 0.5 wt. %. The system further includes a vacuum crystallizer downstream of the evaporator. The vacuum crystallizer is configured to reduce the temperature of the concentrated reaction solution to form pentaerythritol crystals in suspension while retaining the sodium formate in solution. Finally, the system includes a filtration system downstream of the vacuum crystallizer. The filtration system is configured to remove the pentaerythritol crystals in suspension to create a mother liquor comprising the sodium formate in solution.

According to another aspect, a drilling fluid composition includes a base fluid; one or more additives chosen from an emulsifier, a fluid-loss control additive, or an alkaline compound; and 100 to 200 pounds per barrel (lb/bbl) of sodium formate having a purity in excess of 99.5 wt. %.

Additional features and advantages of the described embodiments will be set forth in the detailed description which follows, and in part will be readily apparent to those skilled in the art from that description or recognized by practicing the described embodiments, including the detailed description which follows and the claims.

BRIEF DESCRIPTION OF FIGURES

The following detailed description of the illustrative embodiments can be understood when read in conjunction with the following drawings.

DETAILED DESCRIPTION

Embodiments of the present disclosure are directed to methods of synthesizing ultra-pure sodium formate and additionally to drilling fluid compositions incorporating the sodium formate. The drilling fluid composition comprising the synthesized sodium formate provides beneficial shale stabilization for water sensitive clay or shale formations and clay containing sandstone.

Methods of synthesizing ultra-pure sodium formate include reacting acetaldehyde, formaldehyde, and NaOH to form a raw reaction solution comprising pentaerythritol and sodium formate. The methods further include reducing the water content of the raw reaction solution and removing any unreacted formaldehyde from the raw reaction solution to form a concentrated reaction solution with a formaldehyde concentration less than 0.5% by weight followed by cooling the concentrated reaction solution to form pentaerythritol crystals in suspension while retaining sodium formate in solution. Additionally, the method includes filtering the cooled concentrated reaction solution to remove the pentaerythritol crystals and create a mother liquor comprising the sodium formate in solution and separating the sodium formate from the mother liquor to collect the ultra-pure sodium formate having a purity greater than 99.5%.

Figure 1:
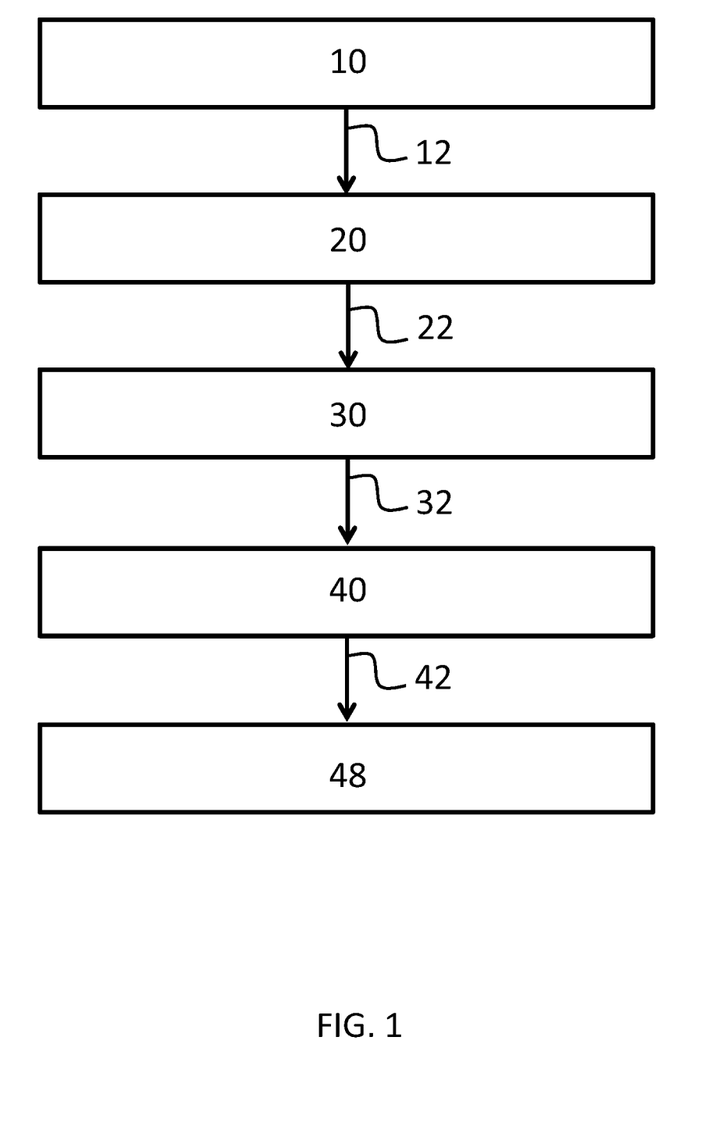
FIG. 1 provides a flow chart of a method to synthesize sodium formate in accordance with one or more embodiments of the disclosure.
Figure 2:
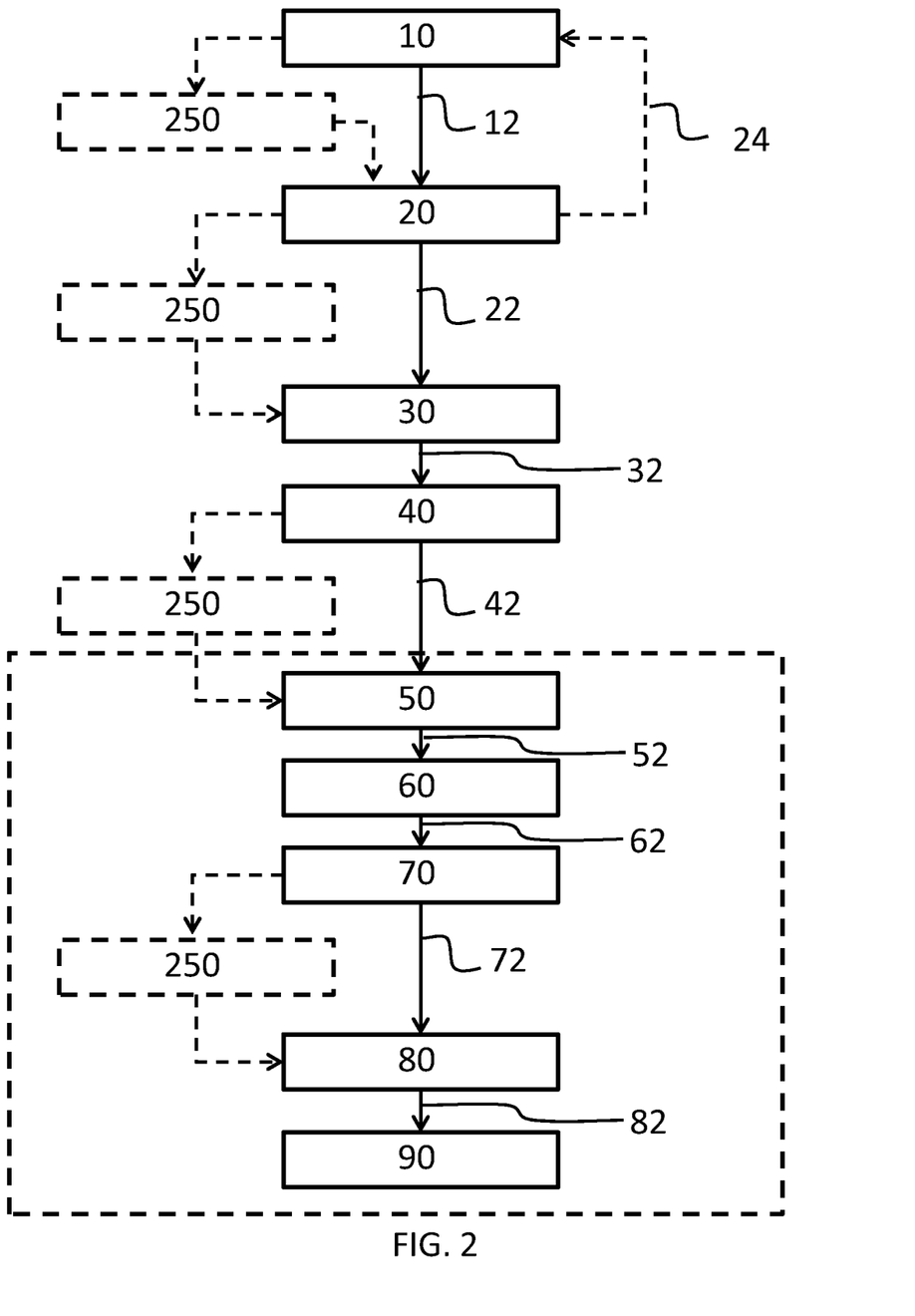
FIG. 2 provides a flow chart of a method to synthesize sodium formate in accordance with one or more embodiments of the disclosure.

With reference to FIGS. 1 and 2, the synthesis of the sodium formate initially includes a reaction step 10. The reaction step 10 comprises the reaction of acetaldehyde, formaldehyde, and NaOH to form a raw reaction solution 12 comprising pentaerythritol and sodium formate. The overall reaction comprises formaldehyde and acetaldehyde in the presence of sodium hydroxide in a 4:1:1 molar ratio to produce pentaerythritol and sodium formate in accordance with Reaction (1). For each mole of acetaldehyde and sodium hydroxide reacted, one mole of pentaerythritol and sodium formate are produced.

$$CH_3CHO + 4CH_2O + NaOH \rightarrow C(CH_2OH)_4 + HCOONa \quad \text{Reaction (1)}$$

Reaction (1) is completed in a step-wise manner in accordance with the sub-reactions of Reaction (2), Reaction (3), Reaction (4), and Reaction (5). Specifically, acetaldehyde and formaldehyde in the presence of an alkaline condensation agent react to form $(HOCH_2)_3CCHO$ [tris(hydroxymethyl)ethanol]. The $(HOCH_2)_3CCHO$ is formed through an Aldol condensation reaction with three successive molecules of formaldehyde added to one molecule of acetaldehyde. The sequential reactions of Reaction (2), Reaction (3), and Reaction (4) forms the $(HOCH_2)_3CCHO$. As such, the acetaldehyde and the formaldehyde may be initially reacted in a 3:1 molar ratio.

$$CH_3CHO + CH_2O \rightarrow HOCH_2—CH_2CHO \quad \text{Reaction (2)}$$

$$CHOCH_2—CH_2CHO + CH_2O \rightarrow (HOCH_2)_2CHCHO \quad \text{Reaction (3)}$$

$$(HOCH_2)_2CHCHO + CH_2O \rightarrow (HOCH_2)_3CCH \quad \text{Reaction (4)}$$

The $(HOCH_2)_3CCHO$ ultimately formed in Reaction (4) is reacted with formaldehyde and NaOH to form the pentaerythritol and the sodium formate in accordance with Reaction (5). The formation of the pentaerythritol and the sodium formate is in accordance with a crossed Cannizaro reaction of the $(HOCH_2)_3CCHO$ with the formaldehyde and NaOH. As such, the $(HOCH_2)_3CCHO$, the formaldehyde, and the NaOH may be reacted in a 1:1:1 molar ratio.

$$(HOCH_2)_3CCHO + CH_2O + NaOH \rightarrow C(CH_2OH)_4 + HCOONa \quad \text{Reaction (5)}$$

In one or more embodiments, the reaction step 10 further includes providing formic acid to the raw reaction solution 12. The formic acid deactivates or neutralizes any excess NaOH in the raw reaction solution 12 at the end of the reaction synthesis. The result is the raw reaction solution 12 obtains a slightly acidic potential of hydrogen (pH); that is a pH less than 7.0.

In accordance with Reaction (1), to produce 1 mole of pentaerythritol requires 4 moles of formaldehyde. In one or more embodiments, excess formaldehyde, such as 8.5 to 9 moles of formaldehyde, may be provided to achieve maximum yield of mono pentaerythritol. With 8.5 moles of formaldehyde provided, 4 moles of formaldehyde are consumed in accordance with Reaction (1) with 3.5 moles of formaldehyde remaining in excess at completion of the reaction. Additionally, Reaction (1) of reaction step 10 may not behave as a perfect reaction. Specifically, side reactions and incomplete Reactions (2)-(4) may result in excess formaldehyde at the completion of the reaction step 10. The acetaldehyde is consumed fully in reaction step 10 leaving excess NaOH and formaldehyde. The excess NaOH may be neutralized with the addition of formic acid. In one or more embodiments, the formaldehyde in excess may represent approximately 7.5% of the total volume of the raw reaction solution 12.

The synthesis of the ultra-pure sodium formate additionally includes an evaporative stripping step 20. The evaporative stripping step 20 comprises reducing the water content and formaldehyde concentration of the raw reaction solution 12. Formaldehyde may be removed through the evaporative stripping until a concentrated reaction solution 22 is formed which is substantially free from formaldehyde. Specifically, water removal in the evaporative stripping step 20 generates the concentrated reaction solution 22 which is saturated with pentaerythritol. In various embodiments, the concentrated reaction solution 22 comprises less than 0.5 wt. % formaldehyde, less than 0.3 wt. % formaldehyde, less than 0.2 wt. % formaldehyde, less than 0.1 wt. % formaldehyde, or less than 0.05 wt. % formaldehyde. An elevated formaldehyde content in the concentrated reaction solution 22 may lead to undesirable coloration, poor crystallization, other undesirable characteristics, or combinations thereof upon further processing of the concentrated reaction solution 22. The evaporative stripping step 20 also generates an evaporate stream 24 comprising the water, formaldehyde, and methanol removed from the raw reaction solution 12.

The synthesis of the sodium formate further includes a pentaerythritol crystallization step 30. The pentaerythritol crystallization step 30 comprises cooling the concentrated reaction solution 22 to form pentaerythritol crystals in suspension while retaining the sodium formate in solution. In various embodiments, the concentrated reaction solution 22 is cooled to less than 50° C., less than 45° C., less than 37° C., or less than 15° C. to initiate pentaerythritol crystal formation and generate a crystallized pentaerythritol solution 32.

With continued reference to FIGS. 1, 2, in a pentaerythritol removal step 40 the method comprises filtering the crystallized pentaerythritol solution 32 to remove the pentaerythritol crystals. The remainder upon removal of the pentaerythritol crystals from the crystallized pentaerythritol solution 32 is a mother liquor 42 comprising the sodium formate in solution.

Further, sodium formate is separated from the mother liquor 42 in a sodium formate separation step 48. With reference to FIG. 2, the sodium formate separation step 48 may include a solvent extraction step 50 in which an extraction solvent is utilized for sodium formate recovery. In one or more embodiments, the extraction solvent is isobutanol. The isobutanol acts as a solvent to separate the sodium formate from the remainder of the mother liquor 42 and generate a sodium formate rich solvent stream 52 comprising the extraction solvent and sodium formate.

In one or more embodiments, the extraction solvent is separated from the sodium formate rich solvent stream 52 in a solvent recovery step 60. Removing the extraction solvent from the sodium formate rich solvent stream 52 provides a purified sodium formate stream 62. The extraction solvent is separated from the remainder of the sodium formate rich solvent stream 52 by introducing the sodium formate rich solvent stream 52 to a reduced pressure environment. The reduced pressure environment results in the isobutanol or other extraction solvent vaporizing from the sodium formate rich solvent stream 52 leaving the purified sodium formate stream 62 comprising water and sodium formate.

In one or more embodiments, methods of synthesizing ultra-pure sodium formate may include processing the purified sodium formate stream 62 to remove water in a water extraction step 70. Water may be removed from the purified sodium formate stream 62 to form a sodium formate suspension 72. Generation of the sodium formate suspension 72 by reducing the water content of the purified sodium formate stream 62 forms crystallized sodium formate. In one or more embodiments, the crystallized sodium formate may be separated from the liquid components of the sodium formate suspension 72 in a sodium formate separation step 80. The sodium formate separation step 80 may include filtration of the crystallized sodium formate, complete evaporation of the water in the sodium formate suspension 72, or other separation technique known to those skilled in the art.

With continued reference to FIGS. 1 and 2, in one or more embodiments, the method of synthesizing ultra-pure sodium formate may include drying the sodium formate recovered in the sodium formate separation step 80 in a sodium formate drying step 90. The moisture content in the sodium formate may be reduced to less than 3 percent by weight on a dry basis, less than 2 percent by weight on a dry basis, less than 1 percent by weight on a dry basis, or less than 0.5 percent by weight on a dry basis.

In various embodiments, buffer tanks (not shown) are provided between process steps and associate systems to maintain the pH of the various process streams in buffer steps 250 as illustrated in FIG. 2.

The ultra-pure sodium formate formed according to embodiments of this disclosure may comprise traces of impurities. The impurities may include sulfur, magnesium, aluminum, chlorine, potassium, iron, nickel, pentaerythritol, and cyclic pentaerythritol formal in pure forms, as oxides, or as parts of compounds. In one or more embodiments, the sodium formate comprises a minimum purity of 99.5 wt. %, that is the sodium formate may comprise up to 0.5% by weight of the impurities. In various embodiments, the sodium formate comprises a minimum purity of 99.7 wt. %, a minimum purity of 99.9 wt. %, a minimum purity of 99.95 wt. %, or a minimum purity of 99.99 wt. %.

Figure 3:
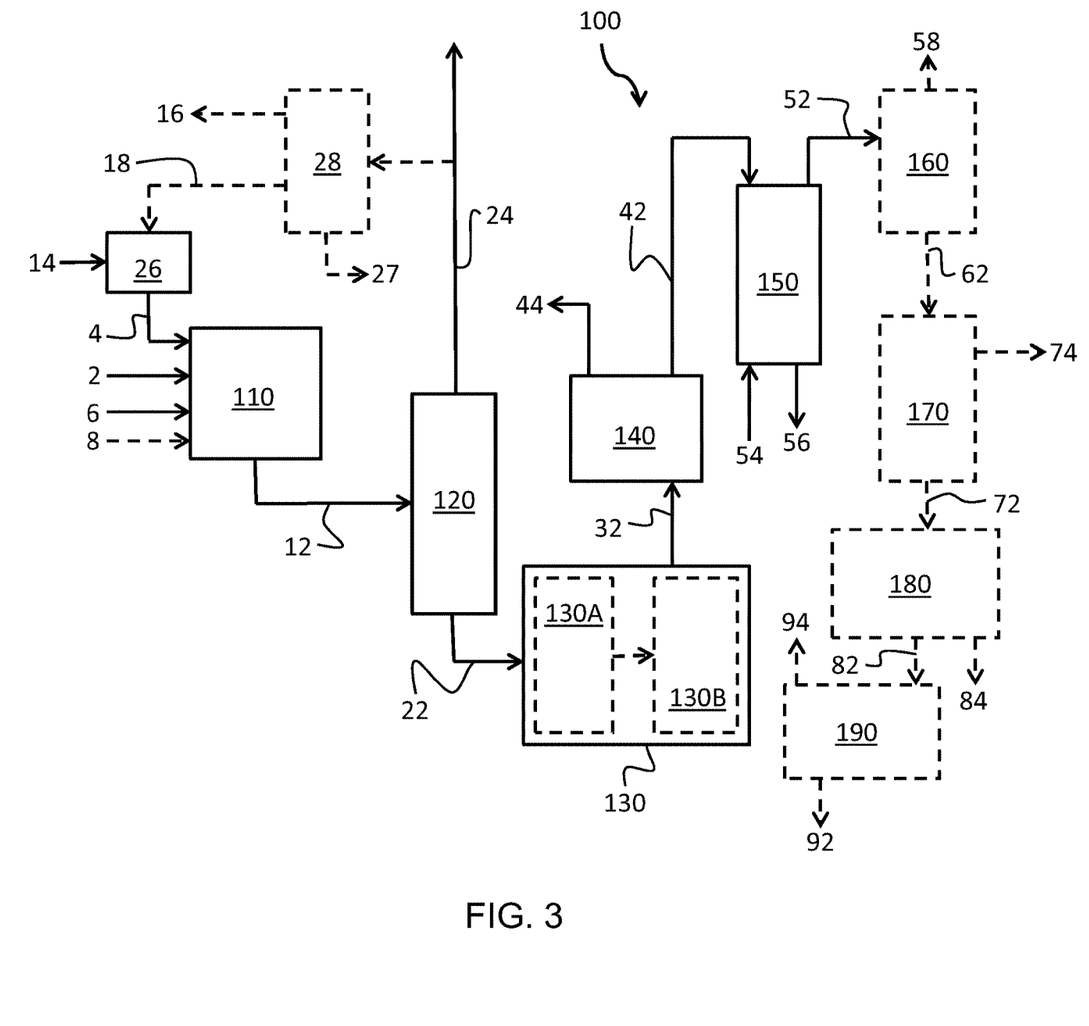
FIG. 3 provides a schematic of a system for synthesizing ultra-pure sodium formate in accordance with one or more embodiments of the present disclosure.

With reference to FIG. 3, a system for synthesis of ultra-pure sodium formate 100 includes a reaction vessel 110 for completion of the reaction step 10. The reaction step 10 comprises the reaction of acetaldehyde, formaldehyde, and NaOH provided in an acetaldehyde stream 2, a formaldehyde stream 4, and a NaOH stream 6 respectively. The reaction of the acetaldehyde stream 2, the formaldehyde stream 4, and the NaOH stream 6 produces the raw reaction solution 12 comprising pentaerythritol and sodium formate.

The formaldehyde, acetaldehyde, and NaOH may be provided for the reaction step 10 in varying ratios. In one or more embodiments, the acetaldehyde stream 2, the formaldehyde stream 4, and the NaOH stream 6 are provided in a 1:9:1.12 molar ratio. In various embodiments, the molar ratio of formaldehyde to acetaldehyde provided to the reaction vessel 110 for reaction may be between 4:1 and 15:1, 5:1 and 12:1, 6:1 and 10:1, or 7:1 and 9:1 and a molar ratio of NaOH to acetaldehyde may be between 1:1 and 1.5:1, 1:1 and 1.25:1, 1:1 and 1.2:1, or 1.1:1 and 1.2:1. Without wishing to be bound by theory, it is believed that maximum formation of pentaerythritol in the reaction vessel 110 is achieved with a molar ratio of formaldehyde to acetaldehyde of approximately 9:1 and a molar ratio of NaOH to acetaldehyde of approximately 1.12:1.

The reaction of the acetaldehyde stream 2, the formaldehyde stream 4, and the NaOH stream 6 in the reaction vessel 110 is completed at an elevated reaction temperature. The acetaldehyde may be added to the reactor in limited quantities through a sparger ring. In various embodiments, the reaction is completed at a reaction temperature of 40 to 70° C., 45 to 65° C., 50 to 60° C., or 52 to 58° C. During reaction, the reactants are mixed in the reaction vessel 110. It will be appreciated that reaction temperatures in excess of 70° C. or less than 40° C. may result in an ultimately lower pentaerythritol yield.

In one or more embodiments formic acid in a formic acid stream 8 may additionally be provided to the reaction vessel 110 along with the acetaldehyde, formaldehyde, and NaOH. Specifically, the formic acid may be provided to the reaction vessel 110 to deactivate or neutralize any excess NaOH in the raw reaction solution 12 at the end of the reaction synthesis. The result is the raw reaction solution 12 obtains a slightly acidic pH. In further embodiments, the raw reaction solution is transferred to a second reaction vessel (not shown) where the formic acid stream 8 is fed to deactivate or neutralize any excess NaOH in the raw reaction solution 12. As the overall reaction comprises formaldehyde and acetaldehyde in the presence of sodium hydroxide in a 4:1:1 molar ratio to produce pentaerythritol and sodium formate in accordance with Reaction (1), the amount of formic acid necessary to neutralize residual NaOH may be determined based on the molar ratio of constituents fed to the reaction vessel 110 in the acetaldehyde stream 2, the formaldehyde stream 4, and the NaOH stream 6. It is expected that the raw reaction solution will comprise approximately 0.11 to 0.15 wt. % NaOH. With a batch size of approximately 82.0 metric tons, 180 kilograms (kg) to 200 kg of formic acid would neutralize the excess caustic (NaOH) at the end of reaction.

With continued reference to FIG. 3, the raw reaction solution 12 is transferred to an evaporator 120 to reduce the water content of the raw reaction solution 12 as well as remove residual formaldehyde from the raw reaction solution 12 not reacted in the reaction step 10. In one or more embodiments, a first stage of the evaporator 120 may serve as a formaldehyde stripper to remove formaldehyde from the raw reaction solution 12. As water is evaporated from the raw reaction solution 12 other volatile components are removed as well. Repeated and continuous operation of the evaporator 120 reduces the water content of the raw reaction solution 12 to near the saturation point for pentaerythritol. Additionally, the concentration of formaldehyde is reduced in conjunction with the reduction in water concentration. As previously indicated, formaldehyde concentration in the concentrated reaction solution 22 may be reduced to less than 0.5 wt. % formaldehyde, less than 0.3 wt. % formaldehyde, less than 0.2 wt. % formaldehyde, less than 0.1 wt. % formaldehyde, or less than 0.05 wt. % formaldehyde. Additionally, methanol introduced with the formaldehyde stream 4 or synthesized as a side product in the reactions for generating the sodium formate is removed by the evaporator 120.

Various streams are produced in the evaporator 120 for further processing. In one or more embodiments, the evaporator 120 produces a stream of the concentrated reaction solution 22 generated from reducing the water, formaldehyde, and methanol content of the raw reaction solution 12. The evaporator 120 also generates the evaporate stream 24 comprising the water, formaldehyde, and methanol removed from the raw reaction solution 12.

In one or more embodiments, the evaporate stream 24 may be recycled for utilization in formaldehyde blending. Specifically, the evaporate stream 24 which comprises the unreacted formaldehyde removed from the raw reaction solution 12 may be mixed with formaldehyde of a greater concentration to generate formaldehyde of desired concentration for the reaction step 10. For example, the evaporate stream 24 may comprise 8 to 9 wt. % formaldehyde which may be mixed with a strong formaldehyde solution 14 comprising approximately 48 wt. % formaldehyde to generate the final formaldehyde stream 4 comprising 15 to 16 wt. % formaldehyde. In some embodiments, all or a portion of the evaporate stream 24 is provided to a dilute formaldehyde tank 26 for combination with a strong formaldehyde solution 14 to generate the formaldehyde stream 4. In further embodiments, all or a portion of the evaporate stream 24 is mixed in-line with the strong formaldehyde solution to generate the formaldehyde stream 4.

With continued reference to FIG. 3, in one or more embodiments, all or a portion of the evaporate stream 24 may be provided to a stripping unit 28. The stripping unit 28 may separate the evaporate stream 24 into its constituent components. Specifically, the stripping unit may strip methanol from the evaporate stream 24 to generate a concentrated methanol stream 16, strip formaldehyde from the evaporate stream 24 to generate a concentrated formaldehyde stream 18, or both leaving a bottom product 27 of weak aldehydic water. The bottom product in one or more embodiments comprises less than 500 parts per million (ppm) of formaldehyde on a mass basis. The collected methanol and formaldehyde from the concentrated methanol stream 16 and concentrated formaldehyde stream 18 may be sold, utilized in the system 100, or utilized as a feed in another process or system. The bottom product 27 may be collected in a tank and used internally to the system 100 as make-up water and the remainder may be sent to an effluent plant for disposal.

To generate pentaerythritol crystals the concentrated reaction solution 22 is cooled in the pentaerythritol crystallization step 30. As previously indicated, the pentaerythritol crystallization step 30 comprises cooling the concentrated reaction solution 22 to form pentaerythritol crystals in suspension while retaining the sodium formate in solution in the crystallized pentaerythritol solution 32. The concentrated reaction solution 22 may have a temperature of approximately 148° C. when exiting the evaporator 120. In various embodiments, the concentrated reaction solution 22 is cooled with a vacuum crystallizer 130 to less than 50° C., less than 45° C., less than 37° C., or less than 15° C. to initiate pentaerythritol crystal formation to generate the crystallized pentaerythritol solution 32. In one or more embodiments, the vacuum crystallizer 130 comprises two or more crystallizer units in series to generate the suspension containing pentaerythritol crystals. The vacuum crystallizers 130 may be a vacuum draft-tube type crystallizer with a bottom driven agitator. In a first stage of crystallization, the concentrated reaction solution 22 is provided to the first vacuum crystallizer 130A for an initial reduction in temperature. In various embodiments, the first vacuum crystallizer 130A may reduce the concentrated reaction solution 22 to less than 80° C., less than 75° C., less than 70° C., or approximately 65° C. The first vacuum crystallizer 130A may utilize a vacuum pump to maintain the reduced operating temperature. In a second stage of crystallization, the concentrated reaction solution 22 is provided from the first vacuum crystallizer 130A to the second vacuum crystallizer 130B for further temperature reduction and crystallization. The second vacuum crystallizer 130B achieves ultimate temperature reduction to less than 50° C., less than 45° C., less than 37° C., or less than 15° C. to initiate pentaerythritol crystal formation. The second vacuum crystallizer 130B may operate using an ejector vacuum system such as a steam jet ejector system.

With continued reference to FIG. 3, in one or more embodiments, the removal of the pentaerythritol from the crystallized pentaerythritol solution 32 is achieved with a filtration system 140 in the pentaerythritol removal step 40. The filtration system 140 may be a vacuum belt filter. With a vacuum belt filter, the crystallized pentaerythritol solution 32 from the vacuum crystallizer 130 is dewatered on the vacuum belt filter and the pentaerythritol crystals are washed with a mix of filtrates and water. Specifically, the pentaerythritol crystals are retained by the vacuum belt filter and the mother liquor 42 containing the sodium formate in solution is passed through the vacuum belt filter separating the pentaerythritol crystals from the remainder of the crystallized pentaerythritol solution 32. In various embodiments, the filtration system 140 removes at least 80% of the pentaerythritol, at least 85% of the pentaerythritol, at least 90% of the pentaerythritol, or at least 92% of the pentaerythritol from the crystallized pentaerythritol solution 32. The pentaerythritol crystals removed from the crystallized pentaerythritol solution 32 are expelled from the filtration system 140 as a pentaerythritol waste stream 44. It will be appreciated that expeditious filtration and separation of the pentaerythritol crystals from the pentaerythritol solution 32 is advantageous to minimize warming of the pentaerythritol solution 32 and dissolution of the pentaerythritol crystals back into solution thereby decreasing yield.

The mother liquor 42 containing sodium formate and non-crystallizable organics is passed to an extraction tower 150 for separation of the sodium formate and the remainder of the mother liquor 42 in the solvent extraction step 50. The collected pentaerythritol crystals removed by the filtration system 140 may be passed on for further processing.

Separation of the sodium formate and the remainder of the mother liquor 42 in the solvent extraction step 50 includes concurrently feeding the mother liquor 42 and an extraction solvent 54 to the extraction tower 150. In one or more embodiments, the extraction tower 150 comprises a counterflow multistage extraction column. Specifically, the mother liquor 42 is fed to the top of the extraction tower 150 and the extraction solvent 54 is fed to the bottom of the extraction tower 150. The sodium formate is absorbed from the mother liquor 42 into the extraction solvent 54 to form a sodium formate rich extraction solvent stream 52. The remainder of the mother liquor 42 is exhausted from the extraction tower 150 as a mother liquor waste stream 56. The mother liquor waste stream 56 may comprise water penta organics, penta formals, and cyclic penta formals. Subsequently, in the solvent recovery step 60, the sodium formate rich extraction solvent stream 52 is provided to a solvent separator 160 to separate the extraction solvent and the sodium formate. Removing the extraction solvent as an extraction solvent waste stream 58 provides a purified sodium formate stream 62.

The water may be removed from the purified sodium formate stream 62 through any means known to one skilled in the art for removing water from an aqueous solution. In one or more embodiments the purified sodium formate stream 62 is fed to one or more sodium formate crystallizers 170 of a forced circulation design to reduce the water content of the purified sodium formate stream 62 such that the sodium formate suspension 72 and a waste water stream 74 are formed.

With continued reference to FIG. 3, the sodium formate suspension 72 may be provided to a sodium formate crystal separator 180 to separate the sodium formate crystals from the liquid components of the sodium formate suspension 72 in the sodium formate separation step 80. The sodium formate crystal separator 180 may be in accordance with any means for separating a crystallized product from a liquid known to one skilled in the art. In one or more embodiments, the sodium formate crystal separator 180 is a centrifugal separator or specifically a screen scroll separator. A screen scroll separator is a filtering centrifuge which separates solids and liquid from a solid-liquid mixture where the solid material is retained on a screen and is moved along the screen via an internal screw conveyor while the liquid output is obtained due to centrifugal force causing the feed slurry to pass through the screen openings. The sodium formate suspension 72 is fed to the centrifugal separator which spins to separate the various constituents of the sodium formate suspension 72 based on their liquid or solid nature. Specifically, wet sodium formate 82 is substantially separated from the liquid constituents of the sodium formate suspension 72. The liquid constituents of the sodium formate suspension 72 are exhausted as a sodium formate suspension waste stream 84.

In one or more embodiments, the wet sodium formate 82 may be passed to a dryer 190 to reduce the water content of the sodium formate providing removed water 94 and the ultra-pure sodium formate 92. In various embodiments, the dryer 190 may be a heated vessel such as a kiln, tunnel furnace, or oven to remove residual water. The moisture content in the ultra-pure sodium formate 92 may be reduced to less than 1 wt. % on a dry basis, less than 0.5 wt. % on a dry basis, less than 0.1 wt. % on a dry basis, or less than 0.05 wt. % on a dry basis.

In one or more embodiments, the pentaerythritol waste stream 44 of the pentaerythritol removed from the concentrated reaction solution 22 in the filtration system 140 is collected for further processing. Secondary processing of the pentaerythritol waste stream 44 is completed to separate impurities and water from the pentaerythritol. The collected pentaerythritol crystals from the filtration system 140 may be dissolved with water to form a purified pentaerythritol solution. The purified pentaerythritol solution may comprise approximately 35% pentaerythritol with the substantial reminder comprising water. The purified pentaerythritol solution is buffered in a tank (not shown) and then decolored by passing it through active carbon towers (not shown), and through a set of ion exchangers (not shown) which removes any remaining sodium ions. In various embodiments the coloration of the final pentaerythritol crystals is less than or equal to 5, less than or equal to 4, or less than or equal to 3 in accordance with American Society for Testing & Materials (ASTM) Standard Test Method for Color of Pine Chemicals and Related Products (Instrumental Determination of Gardner Color)—ASTM D6166-12(2016). Subsequently, the purified pentaerythritol solution is cooled to less than 40° C. in a crystallizer (not shown) equipped with a heater to evaporate a portion of the water in the purified pentaerythritol solution. The resulting solution comprises pentaerythritol of elevated purity in a suspension which may be fed to a vacuum belt filter (not shown), for example, for separation. The separated pentaerythritol crystals may then be dried in a dryer (not shown).

In some embodiments, a buffer tank (not shown) is provided between the reaction vessel 110 and the evaporator 120 to maintain the pH of the raw reaction solution 12. In some embodiments, a buffer tank is provided between the evaporator 120 and the vacuum crystallizer 130 to maintain the pH of the concentrated reaction solution 22. In some embodiments, a buffer tank is provided between the filtration system 140 and the extraction tower 150 to maintain the pH of the mother liquor 42.

The synthesized ultra-pure sodium formate may be utilized in a drilling fluid. An example drilling fluid composition incorporating the sodium formate includes a base fluid and one or more additives including emulsifiers, weighting material, viscosifiers, fluid-loss control additives, or alkaline compounds.

Drilling fluids include drilling muds, workover fluids, and completion fluids. As used in this disclosure, "drilling fluid" means any fluid used to aid the drilling of boreholes into subterranean formations. As used in this disclosure, "completion fluids" are solids-free liquid used to "complete" an oil or gas well. Specifically, this fluid is placed in the well to facilitate final operations prior to initiation of production, such as setting screens production liners, downhole valves or shooting perforations into the producing zone. The fluid is meant to control a well should downhole hardware fail, without damaging the producing formation or completion components. As used in this disclosure, "workover fluids" are fluids used during that is used during workover operations of a wellbore such as during repair or stimulation of an existing production well for the purpose of restoring, prolonging or enhancing the production of hydrocarbons from the production well. Generically, drilling fluids serve a number of functions with different types specializing in a particular function or functions. In one or more embodiments, the drilling fluid composition assists in the removal of cuttings from the bottom of a borehole during drilling operations. The drilling fluid composition suspends the cuttings and weighted material transports the cutting to the borehole surface with the drilling fluid composition. Additionally, the drilling fluid composition may absorb gases in the borehole, such as carbon dioxide ($CO_2$), hydrogen sulfide ($H_2S$), and methane ($CH_4$), and transport them to the borehole surface for release, sequestration, or burn-off. In further embodiments, the drilling fluid composition also provides a cooling and lubrication functionality for cooling and lubrication of the bit and drill string utilized in boring operations. The drilling fluid composition additionally provides buoyancy to the drill string relieving the tension on the drill string as the length of the borehole increases. In embodiments, the drilling fluid composition also controls subsurface pressures. Specifically, the drilling fluid composition provides hydrostatic pressure in the borehole to provide support to the sidewalls of the borehole and prevent the sidewalls from collapsing and caving in on the drill string. Additionally, the drilling fluid composition provides hydrostatic pressure in the bore to prevent fluids in the downhole formations from flowing into the borehole during drilling operations.

Operational conditions affect the properties of the drilling fluid. For example, interaction of a drilling fluid with a formation having swelling clay, excessive solids content, or both, or subjecting the drilling fluid to extreme downhole temperatures. The temperatures, which range from surface temperature (ambient temperature) up to 500° F. (260° C.), may cause the drilling fluid to thicken or thin, excessively increase or decrease in viscosity, or any combination of these. In some drilling scenarios, a drilling fluid having an increased density, and therefore increased solids content, may enable drilling of a pressurized formation or may be used to control and kill a flowing downhole formation. A flowing downhole formation refers to a formation in which the fluid in the formation is flowing into the wellbore. The increased concentration of solids and increased density of the drilling fluids used in these applications increase the ability of the drilling fluids to support the wellbore and provide enhanced hydrostatic pressure to prevent fluids in the formation from flowing into the wellbore.

Without wishing to be bound by theory, inclusion of sodium formate is believed to be beneficial to the overall drilling fluid. Sodium formate is highly soluble in water with a solubility of 43.82 grams per 100 milliliters (g/100 mL) at 0° C., 97.2 g/100 mL at 20° C., and 160 g/100 mL at 100° C. Sodium formate brines are non-corrosive organic monovalent fluids. A sodium formate brine provides an increased density compared to tradition divalent chloride and bromide brines and may reach 1.3 specific gravity (10.8 pounds per gallon (ppg)) at saturation. Additionally, sodium formate is 49% weight solvent per weight solution (w/w) soluble in water compared to a traditional divalent chloride and bromide brines which are typically approximately 30% w/w in the density range of sodium formate brine.

Drilling fluids comprising sodium formate also do not interact with reservoir waters to form precipitates. Specifically, as the sodium formate forms non-corrosive organic monovalent fluids the potential for precipitation of carbonate, bicarbonate, or sulphate compounds is reduced or eliminated. Precipitates can damage reservoirs by reducing permeability. Brines formed from traditional formulations with a divalent nature may cause damage through this precipitation mechanism.

As stated previously, the drilling fluid composition includes at least the ultra-pure sodium formate, a base fluid, and one or more additives. In one or more embodiments the drilling fluid composition comprises from 100 to 200 pounds per barrel (lb/bbl) of the ultra-pure sodium formate, based on the total weight of the drilling fluid composition. The ultra-pure sodium formate must be present in sufficient quantity to provide shale stabilization and elimination of precipitation of carbonate, bicarbonate, and sulphate compounds in the drilling formation, but not at an excessive quantity to impede other properties of the drilling fluid composition. Specifically, the amount of ultra-pure sodium formate must be controlled as too little sodium formate will not prevent precipitation of carbonate, bicarbonate, and sulphate compounds nor provide sufficient shale stabilization. In further embodiments, the drilling fluid composition comprises from 120 to 190 lb/bbl, 130 to 185 lb/bbl, 140 to 180 lb/bbl, 150 to 180 lb/bbl, 160 to 175 lb/bbl, or 165 to 170 lb/bbl of the ultra-pure sodium formate.

In one or more embodiments, the drilling fluid composition is substantially free of bromide salts such as sodium bromide or any other types of formates other than sodium formate. Without wishing to be bound by theory, the elimination of bromide salts reduces or eliminates the corrosive effect of the bromide salts.

The base fluid may include one or more of deionized, tap, distilled or fresh waters; natural, brackish and saturated salt waters; natural, salt dome, hydrocarbon formation produced or synthetic brines; filtered or untreated seawaters; mineral waters; and other potable and non-potable waters containing one or more dissolved salts, minerals or organic materials. The drilling fluid composition may include from 150 lb/bbl to 350 lb/bbl, 175 lb/bbl to 325 lb/bbl, 200 lb/bbl to 300 lb/bbl, 225 lb/bbl to 275 lb/bbl, or approximately 250 lb/bbl of water. The water is combined with the sodium formate to form a brine solution. This is done to maintain the osmotic balance between the drilling fluid and the formation. The drilling fluid composition contains an amount of water, which is dependent on application and the desired density of the brine solution.

Other additives may be incorporated into the drilling fluid to enhance one or more characteristics of the drilling fluid. Examples of other additives include, but are not limited to, emulsifiers, fluid-loss control additives, alkaline compounds, viscosifiers, or combinations of these. The drilling fluid may also include pH adjustor, electrolytes, glycols, glycerols, dispersion aids, corrosion inhibitors, defoamers, and other additives or combinations of additives.

The drilling fluid composition may optionally include one or more viscosifiers to impart non-Newtonian fluid rheology to the drilling fluid and to facilitate lifting and conveying rock cuttings to the surface of the wellbore. Examples of viscosifiers may include, but are not limited to, xanthan gum polymer (XC polymer), bentonite, polyacrylamide, polyanionic cellulose, or combinations of these viscosifiers. In some embodiments, the drilling fluid composition may include xanthan gum polymer, which is a polysaccharide secreted by the bacteria *Xanthomonas Campestris* (XC). Some example drilling fluid compositions may optionally include from 0.1 lb/bbl to 10 lb/bbl of a viscosifier. In some embodiments, the drilling fluid compositions includes from 0.1 lb/bbl to 10 lb/bbl of XC polymer, 0.2 lb/bbl to 5 lb/bbl of XC polymer, or 0.3 lb/bbl to 1 lb/bbl of XC polymer. Other suitable viscosifiers may be used in the drilling fluid without deviating from the scope of the present subject matter.

The drilling fluid composition may optionally include one or more alkaline compounds for pH adjustment, which may include lime (calcium hydroxide or calcium oxide), soda ash (sodium carbonate), sodium hydroxide, potassium hydroxide, other strong bases, or combinations thereof. It is noted that conjugate bases to acids with a $pK_a$ of more than about 13 are considered strong bases. The pH may be maintained within a range in order to minimize corrosion caused by the drilling fluid on steel tubulars, tanks, pumps, and other equipment contacting the drilling fluid. Additionally, the alkaline compounds may react with gases, such as $CO_2$ or $H_2S$, encountered by the drilling fluid during drilling operations to prevent the gases from hydrolyzing one or more components of the drilling fluid. Some example drilling fluid compositions may optionally include from 0.1 lb/bbl to 10 lb/bbl of alkaline compounds. In some embodiments, the drilling fluid compositions includes from 0.1 lb/bbl to 10 lb/bbl of soda ash, 0.5 lb/bbl to 5 lb/bbl of soda ash, or 1 lb/bbl to 2 lb/bbl of soda ash.

The drilling fluid composition may optionally include one or more calcium carbonates ($CaCO_3$) of differing sizes. The calcium carbonates may be used as bridging material or loss circulation material. In one or more embodiments, the drilling fluid composition may include a fine $CaCO_3$ having a mass-median diameter (d50) representing the average particle diameter by mass of 20 to 50 millimeters (mm) or approximately 25 mm. In one or more embodiments, the drilling fluid composition may include a medium $CaCO_3$ having a d50 of 150 to 250 mm or approximately 190 mm. It will be appreciated that in embodiments, the drilling fluid composition comprises both fine $CaCO_3$ and medium $CaCO_3$. In various embodiments, the drilling fluid composition may comprise from 0.0 lb/bbl to 100 lb/bbl of fine $CaCO_3$, 5 lb/bbl to 25 lb/bbl of fine $CaCO_3$, 10 lb/bbl to 20 lb/bbl of fine $CaCO_3$, or approximately 16 lb/bbl of fine $CaCO_3$ and additionally or alternatively from 0.0 lb/bbl to 100 lb/bbl of medium $CaCO_3$, 2 lb/bbl to 25 lb/bbl of medium $CaCO_3$, 5 lb/bbl to 15 lb/bbl of medium $CaCO_3$, or approximately 9 lb/bbl of medium $CaCO_3$. Thus, the total $CaCO_3$ may range from 0.0 lb/bbl to 100 lb/bbl of $CaCO_3$ The drilling fluid composition may optionally include sodium bicarbonate. The sodium bicarbonate may be used to convert hard water into soft water. In various embodiments, the drilling fluid composition may comprise from 0.0 lb/bbl to 1 lb/bbl of sodium bicarbonate, 0.1 lb/bbl to 0.5 lb/bbl of sodium bicarbonate, 0.2 lb/bbl to 0.3 lb/bbl of sodium bicarbonate, or approximately 0.25 lb/bbl of sodium bicarbonate.

The drilling fluid composition may optionally include one or more hydrogen sulfide ($H_2S$) scavengers. In one or more embodiments the hydrogen sulfide scavenger may be sodium sulfite. In various embodiments, the drilling fluid composition may comprise from 0.0 lb/bbl to 1 lb/bbl of $H_2S$, 0.1 lb/bbl to 0.8 lb/bbl of $H_2S$, 0.3 lb/bbl to 0.5 lb/bbl of $H_2S$, or approximately 0.4 lb/bbl of $H_2S$.

In one or more embodiments, fluid-loss control additive may be added to the drilling fluid composition to reduce the amount of filtrate lost from the oil-based drilling fluid composition into a subsurface formation. Examples of fluid-loss control additives include organophilic (for example, amine-treated) lignite, bentonite, manufactured polymers, and thinners or deflocculants. The drilling fluid composition may include from 1 lb/bbl to 10 lb/bbl of fluid-loss control additive, from 1 lb/bbl to 5 lb/bbl of fluid-loss control additive, from 1.5 lb/bbl to 8 lb/bbl of fluid-loss control additive, or from 2 lb/bbl to 5 lb/bbl of fluid-loss control additive.

Commercially available example fluid-loss control additives include VERSATROL™, VERSLIG™, ECOTROL™ RD, ONETROL™ HT, EMI 789, and NOVATECH™ F, all commercially available from MI SWACO, Houston, Tex., and ADAPTA® (methylstyrene/acrylate copolymer) and DURATONE® HT (organophilic leonardite fluid loss additive) which are commercially available from Halliburton Energy Services, Inc. In one or more embodiments, the fluid-loss control additive may be a poly anionic cellulose filter control agent such as PAC™-L which is commercially available from Halliburton Energy Services, Inc.

Inclusion of sodium formate in the drilling fluid composition provides the advantage of not requiring the addition of weighting agents to reach a desired fluid density. Specifically, weighting agents such as barite are not necessary to achieve target fluid densities. In various embodiments, the drilling fluid may be prepared at a density of 81 pounds of mass per cubic foot (lbm/ft$^3$). Additionally, the density of the drilling fluid may be adjusted depending on the downhole conditions during drilling operations; specifically, the formation pressure. The density of the drilling fluid may be increased by increasing the sodium formate present in the formulation and the resulting sodium formate brine. Conversely, the density of the drilling fluid may be decreased by diluting the sodium formate brine with additional water.

The drilling fluid composition may have a density of from 30 pounds per cubic foot (lbm/ft$^3$ or pcf) to 81 lbm/ft$^3$, from 40 lbm/ft$^3$ to 81 lbm/ft$^3$, from 50 lbm/ft$^3$ to 81 lbm/ft$^3$, from 60 lbm/ft$^3$ to 81 lbm/ft$^3$, or from 65 lbm/ft$^3$ to 81 lbm/ft$^3$, where 1 lbm/ft$^3$ is approximately 16.02 kilograms per cubic meter (kg/m$^3$). In some embodiments, the drilling fluid composition may have a density that is approximately equal to 70 lbm/ft$^3$ (1,121 kg/m$^3$).

During circulation of the drilling fluid composition through the wellbore, the drilling fluid composition accumulated cuttings and other solids. Additionally, the drilling fluid itself has solids dispersed throughout, such as the sodium formate. During circulation of the drilling fluid composition the solids are continuously mixed and suspended within the drilling fluid composition. However, when circulation of the drilling fluid composition is interrupted or terminated the solids may settle or separate from the bulk of the drilling fluid composition based on the rheology of the drilling fluid composition. Settling of the cuttings and other solids in undesirable because they would accumulate at the bottom of the wellbore and potentially prevent the drill from rotating or completely block the flow path of the drilling fluid composition upon resumption of drilling activities. In an attempt to avoid setting and separation of solids upon interruption of circulation of the drilling fluid composition, the drilling fluid composition may have a yield point of from 8 pounds of force per 100 square feet (lb$_f$/100 ft$^2$) (3.83 Pa) to 30 lb$_f$/100 ft$^2$ (14.36 Pa) and a low shear yield point of from 5 lb$_f$/100 ft$^2$ (2.39 Pa) to 12 lb$_f$/100 ft$^2$ (5.74 Pa), where 1 lb$_f$/100 ft$^2$ is approximately 0.48 Pascal (Pa). The elevated yield point and low shear yield point assists in ensuring the drilling fluid composition gels upon interruption of circulation of the drilling fluid composition and thereby entrains the solids within the gel formation to prevent settling.

The viscosity of the drilling fluid composition may be measured using a standard oilfield viscometer according to test methods provided in the American Petroleum Institute (API) Recommended Practice For Field Testing Oil-Based Drilling Fluids (RP 13B-2/ISO 10414-1:2002) published August 2014 and incorporated by reference into this disclosure in its entirety. Drilling fluid is placed in an annular space between two concentric cylinders. The outer cylinder is rotated at a constant rotational velocity which produces a torque on the inner cylinder (or spindle) which is measured. The viscosity is reported as shear stress in units of pounds of force per 100 square feet (lb$_f$/100 ft$^2$). The viscometer, which may be a Fann 35 from FANN Instruments, may be used to measure the shear rate of the drilling fluid compositions.

The gel strength refers to the shear stress of the drilling fluid measured at a low shear rate following a defined period of time during which the drilling fluid is maintained in a static state. The shear stress at low shear rate may be measured using a standard oilfield viscometer operated at low rpms, such as at 3 rotations per minute (rpm), according to the test methods described in API RP 13B-2. To measure the gel strength, the drilling fluid is first stirred by contacting the drilling fluid with the spindle of the viscometer and operating the viscometer at 600 rpm for 10 seconds. The viscometer is then turned off for a period of time (time period). For a 10 second gel strength, the time period is 10 seconds, and for a 10 minute gel strength, the time period is 10 minutes. Other time periods for measuring gel strength are contemplated. During the time period, the drilling fluid comes to rest in a static state. Upon expiration of the time period, the viscometer is turned back on at a low speed, such as 3 rpm, to generate a low shear rate. The viscometer reading is then taken. The gel strength is reported in units of pounds of force per 100 square feet (lb$_f$/100 ft$^2$).

The 10 second gel strength provides an indication of the ability of the drilling fluid composition to gel immediately upon termination of drill rotation and circulation of the drilling fluid composition. Quick or near instantaneous gelling of the drilling fluid composition upon termination of circulation helps ensure solids do not settle before gelling. A sufficiently high 10 second gel strength indicates the drilling fluid composition formed a robust gel quickly after removal of agitation. The drilling fluid compositions, may have a 10 second gel strength of from 1 lb/100 ft$^2$ to 25 lb/100 ft$^2$, from 2 lb/100 ft$^2$ to 20 lb/100 ft$^2$, from 3 lb/100 ft$^2$ to 15 lb/100 ft$^2$, from 4 lb/100 ft$^2$ to 10 lb/100 ft$^2$, or from 4.5 lb/100 ft$^2$ to 5.5 lb/100 ft$^2$. In one or more embodiments, the drilling fluid compositions may have a 10 second gel strength of approximately 5 lb/100 ft$^2$.

Similarly, the 10 minute gel strength provides an indication of the ability of the drilling fluid composition to sustain a gelled configuration for a sustained period after termination of drill rotation and circulation of the drilling fluid composition. A sufficiently high 10 minute gel strength indicates the drilling fluid composition formed a robust gel which was maintained during periods without agitation. The drilling fluid compositions, may have a 10 minute gel strength of 5 lb/100 ft$^2$ to 40 lb/100 ft$^2$, from 6 lb/100 ft$^2$ to 30 lb/100 ft$^2$, from 7 lb/100 ft$^2$ to 25 lb/100 ft$^2$, from 8 lb/100 ft$^2$ to 20 lb/100 ft$^2$, from 9 lb/100 ft$^2$ to 15 lb/100 ft$^2$, or from 9.5 lb/100 ft$^2$ to 10.5 lb/100 ft$^2$. In one or more embodiments, the drilling fluid composition may have a 10 minute gel strength of approximately 10 lb/100 ft$^2$.

The drilling fluid composition behaves as a rigid body at low stress, but flows as a viscous fluid at greater shear stress. The rheology of the drilling fluid composition may be modeled based on Bingham plastic flow behavior. Additionally, the rheological behavior of the drilling fluid composition may be determined by measuring the shear stress on the drilling fluid composition at different shear rates, which may be accomplished by measuring the shear stress, the shear rate, or both on the drilling fluid using a viscometer (FANN 35 rheometer) at 3 rpm, 6 rpm, 300 rpm, and 600 rpm. Rheology measurements were done at 120° F. (48.9° C.). The rheology of the drilling fluid composition may be evaluated from the plastic viscosity (PV) and the yield point (YP), which are parameters from the Bingham plastic rheology model. The PV represents the viscosity of the drilling fluid composition extrapolated to infinite shear rate. Further, the PV is related to the resistance of the drilling fluid composition to flow due to mechanical interaction between the solids of the drilling fluid composition. The PV reflects the type and concentration of the solids in the drilling fluid composition, and a lesser PV is preferred. The PV of the drilling fluid composition may be estimated by measuring the shear rate of the drilling fluid composition using the viscometer at spindle speeds of 300 rotations per minute (rpm) and 600 rpm and subtracting the 300 rpm measurement from the 600 rpm measurement according to Equation 1, which is provided infra. The PV is provided in this disclosure in units of centipoise (cP).

$$PV = (600 \text{ rpm reading}) - (300 \text{ rpm reading}) \qquad \text{Equation 1}$$

The YP represents the shear stress which when greater than the drilling fluid composition behaves as a rigid body and lesser than which the drilling fluid composition flows as a viscous fluid. Specifically, the YP represents the amount of stress required to move the drilling fluid composition from a static condition. The YP is expressed as a force per area, such as pounds of force per one hundred square feet (lb/100 ft$^2$). YP provides an indication of the carrying capacity of the drilling fluid composition for rock cuttings through the annulus, which provides an indication the hole-cleaning ability of the drilling fluid composition. Additionally, frictional pressure loss is directly related to the YP. If you have a greater YP, you will have greater pressure loss while the drilling fluid composition is being circulated. A drilling fluid having a YP of equal to or greater than 15 lb/100 ft$^2$ is considered acceptable for drilling. The YP is determined by extrapolating the Bingham plastic rheology model to a shear rate of zero. The YP may be estimated from the PV from Equation 1 by subtracting the PV obtained from Equation 1 from the shear rate of the drilling fluid composition measured at 300 rpm according to Equation 2 provided infra.

$$YP = (300 \text{ rpm reading}) - PV \qquad \text{Equation 2}$$

The yield stress is a parameter obtained from the Herschel Buckley (HB) rheology model. The yield stress may be obtained by fitting the HB model to a shear stress with respect to shear rate curve, which is obtained by plotting the dial readings against the corresponding rpm determined on a standard oilfield viscometer. The yield stress indicates the susceptibility of the drilling fluid composition to have barite sag. A high yield stress value is expected to result in a sag resistant drilling fluid composition. The yield stress of the drilling fluid composition may be estimated by calculating the low shear yield point (LSYP). The LSYP is determined by measuring the shear rate of the drilling fluid composition using the viscometer at spindle speeds of 6 rpm and 3 rpm and subtracting the 6 rpm viscometer measurement from twice the 3 rpm viscometer measurement according to Equation 3, which is provided infra.

$$LSYP = [2 \times (3 \text{ rpm reading})] - (6 \text{ rpm reading}) \qquad \text{Equation 3}$$

The LSYP is expressed as a force per area, such as pounds of force per one hundred square feet (lb/100 ft$^2$). A drilling fluid having a LSYP of equal to or greater than 5 lb/100 ft$^2$ is considered acceptable for a drilling fluid.

Examples

The following examples illustrate one or more additional features of the present disclosure. It should be understood that these examples are not intended to limit the scope of the disclosure or the appended claims in any manner.

A drilling fluid was prepared in accordance with embodiments of this disclosure. The components of the drilling fluid of Formulation 1 were added to a vessel and thoroughly mixed. Specifically, water and soda ash were added to a vessel and thoroughly mixed for a period of 5 minutes. Subsequently, sodium formate was added and mixed for 5 minutes followed by the addition of XC polymer and a 10 minute mixing period. Then PAC™-L was added and mixed for 5 minutes. Subsequently, sodium bicarbonate was added followed by a 5 minutes mixing period, fine CaCO$_3$ was added followed by a 2 minutes mixing period, medium CaCO$_3$ was added followed by a 2 minutes mixing period, and finally sodium sulfite was added followed by a 2 minutes mixing period. The formulation of Formulation 1 is listed in Table 1 subsequently provided.

TABLE 1

Drilling Fluid Formulation for Formulation 1

| Ingredient | Formulation 1 Pounds Per Barrel (lb/bbl) |
|---|---|
| Water | 250.1 |
| Soda ash | 0.3 |
| Sodium formate | 167.8 |

TABLE 1-continued

Drilling Fluid Formulation for Formulation 1

| Ingredient | Formulation 1 Pounds Per Barrel (lb/bbl) |
|---|---|
| XC polymer | 0.5 |
| PAC ™ - L | 4 |
| Sodium bicarbonate | 0.25 |
| CaCO₃ (fine) | 16 |
| CaCO₃ (medium) | 9 |
| Sodium sulfite | 0.4 |
| TOTAL | 448.35 |

A drilling fluid designated as Example 1 was prepared in accordance with Formulation 1 where the sodium formate was the ultra-pure sodium formate synthesized in accordance with the present disclosure. The test drilling fluid of Example 1 was prepared for evaluation of viscosity, gel strength, PV, YP, and LSYP according to the methods previously described in this disclosure. The results of these measurements for the invert emulsion drilling fluid of Example 1 are provided in Table 2.

TABLE 2

Evaluation of the Properties of the Test Drilling Fluid

|  | Example 1 |
|---|---|
| 600 rpm viscometer reading | 105 |
| 300 rpm viscometer reading | 67 |
| 200 rpm viscometer reading | 51 |
| 100 rpm viscometer reading | 33 |
| 6 rpm viscometer reading | 7 |
| 3 rpm viscometer reading | 4 |
| 10 second gel strength (lb/100 ft²) | 5 |
| 10 minute gel strength (lb/100 ft²) | 10 |
| PV (cP) | 38 |
| YP (lb/100 ft²) | 29 |
| LSYP (lb/100 ft²) | 1 |

High temperature high pressure (HTHP) performance testing was also completed for Example 1 in accordance with Recommended Practice for Field Testing Water-based Drilling Fluids (API 13B-1).

The drilling fluid of Example 1 utilizing the ultra-pure sodium formate synthesized in accordance with the present disclosure exhibited a HTHP fluid loss of 4 milliliters (ml). Conversely, a drilling fluid utilizing commercially available sodium formate with a purity of 98% would be expected to exhibited a HTHP fluid loss of 20 ml. Minimizing HTHP fluid loss of a drilling fluid is desirable in well construction because it has direct correlation with the cost of maintaining the drilling fluid and success of drilling the well. Lower HTHP fluid loss helps to minimize hole instability, minimize filtrate invasion, and prevents differential sticking.

It should be understood that any two quantitative values assigned to a property may constitute a range of that property, and all combinations of ranges formed from all stated quantitative values of a given property are contemplated in this disclosure. It should be appreciated that compositional ranges of a chemical constituent in a composition or formulation should be appreciated as containing, in some embodiments, a mixture of isomers of that constituent. It should be appreciated that the examples supply compositional ranges for various compositions, and that the total amount of isomers of a particular chemical composition can constitute a range.

It should be understood that any indication of "comprising" also implicitly includes the cases of "consisting of" and "consisting essentially of" and any indication of "comprises" also implicitly includes the cases of "consists of" and "consists essentially of".

Having described the subject matter of the present disclosure in detail and by reference to specific embodiments, it is noted that the various details described in this disclosure should not be taken to imply that these details relate to elements that are essential components of the various embodiments described in this disclosure, even in cases where a particular element is illustrated in each of the drawings that accompany the present description. Rather, the claims appended hereto should be taken as the sole representation of the breadth of the present disclosure and the corresponding scope of the various embodiments described in this disclosure. Further, it should be apparent to those skilled in the art that various modifications and variations can be made to the described embodiments without departing from the spirit and scope of the claimed subject matter. Thus it is intended that the specification cover the modifications and variations of the various described embodiments provided such modification and variations come within the scope of the appended claims and their equivalents.

What is claimed is:

1. A system for synthesizing ultra-pure sodium formate, the system comprising:
  a reaction vessel comprising one or more inlets connected to an acetaldehyde feed stream, a formaldehyde feed stream, and a NaOH feed stream, the reaction vessel configured to react acetaldehyde, formaldehyde, and NaOH from the acetaldehyde feed stream, the formaldehyde feed stream, and the NaOH feed stream respectively to form a raw reaction solution comprising pentaerythritol and sodium formate;
  an evaporator downstream of the reaction vessel, the evaporator being configured to reduce the water content of the raw reaction solution and remove unreacted formaldehyde from the raw reaction solution to form a concentrated reaction solution with a formaldehyde concentration less than 0.5% by weight;
  a vacuum crystallizer downstream of the evaporator, the vacuum crystallizer being configured to reduce the temperature of the concentrated reaction solution to form pentaerythritol crystals in suspension while retaining the sodium formate in solution;
  a filtration system downstream of the vacuum crystallizer, the filtration system being configured to remove the pentaerythritol crystals in suspension to create a mother liquor comprising the sodium formate in solution; and
  an extraction tower downstream of the filtration system, the extraction tower being configured to separate the sodium formate from the mother liquor by exposing the mother liquor to an extraction solvent selected to absorb the sodium formate.

2. The system of claim 1 where acetaldehyde, formaldehyde, and NaOH are provided to the reaction vessel as a reaction feed in a formaldehyde to acetaldehyde molar ratio of 4:1 to 15:1 and a NaOH to acetaldehyde molar ratio of 1:1 to 1.5:1.

3. The system of claim 1 where formic acid is additionally provided in a formic acid feed to the reaction vessel to neutralize excess NaOH.

4. The system of claim 1 where the system further comprises a sodium formate crystallizer downstream of the filtration system, the crystallizer configured to reduce the water content of a feed stream to the sodium formate crystallizer such that the sodium formate crystallizes and forms a sodium formate suspension.

5. The system of claim 4 where the system further comprises a sodium formate crystal separator downstream of the sodium formate crystallizer, the sodium formate crystal separator configured to separate the sodium formate crystals from the sodium formate suspension.

6. The system of claim 5 where the sodium formate crystal separator is configured to centrifugally separated the sodium formate crystals from the liquid component of the sodium formate suspension.

7. The system of claim 1 where the system further comprises a dryer downstream of the filtration system, the dryer configured to remove water from a feed stream to the dryer to produce dried sodium formate with a water content of less than 1 percent by weight on a dry basis.

8. The system of claim 1 where the system further comprises a recycle pathway configured to transport formaldehyde removed in the evaporator to the reaction vessel.

* * * * *

UNITED STATES PATENT AND TRADEMARK OFFICE
CERTIFICATE OF CORRECTION

PATENT NO. : 10,577,300 B2
APPLICATION NO. : 16/006225
DATED : March 3, 2020
INVENTOR(S) : Abdullah Al-Yami et al.

Page 1 of 1

It is certified that error appears in the above-identified patent and that said Letters Patent is hereby corrected as shown below:

In the Specification

In Column 3, Line(s) 49, delete "$(HOCH_2)_2CHCHO+CH_2O \rightarrow (HOCH_2)_3CCH$" and insert --$(HOCH_2)_2CHCHO + CH_2O \rightarrow (HOCH_2)_3CCHO$--, therefor.

Signed and Sealed this
Twenty-sixth Day of May, 2020

Andrei Iancu
*Director of the United States Patent and Trademark Office*